US011278258B2

(12) United States Patent
Hashino et al.

(10) Patent No.: US 11,278,258 B2
(45) Date of Patent: Mar. 22, 2022

(54) BIOLOGICAL SOUND MEASURING DEVICE, BIOLOGICAL SOUND MEASUREMENT SUPPORT METHOD, AND BIOLOGICAL SOUND MEASUREMENT SUPPORT PROGRAM

(71) Applicant: OMRON HEALTHCARE CO., LTD., Muko (JP)

(72) Inventors: Kenji Hashino, Kyoto (JP); Kei Asai, Kyoto (JP); Naoto Ohgami, Kyoto (JP); Naoki Matsumoto, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 17/060,167

(22) Filed: Oct. 1, 2020

(65) Prior Publication Data
US 2021/0015443 A1 Jan. 21, 2021

Related U.S. Application Data

(63) Continuation of application No. PCT/JP2019/015676, filed on Apr. 10, 2019.

(30) Foreign Application Priority Data

Apr. 13, 2018 (JP) .............................. JP2018-078018

(51) Int. Cl.
*H04R 29/00* (2006.01)
*A61B 7/04* (2006.01)
(Continued)

(52) U.S. Cl.
CPC .............. *A61B 7/04* (2013.01); *G08B 21/182* (2013.01); *G10L 25/66* (2013.01)

(58) Field of Classification Search
CPC ..................................................... H04R 29/00
See application file for complete search history.

(56) References Cited

U.S. PATENT DOCUMENTS 5,602,924 A * 2/1997 Durand .................. A61B 7/005
381/67
5,812,678 A * 9/1998 Scalise .................. A61B 7/003
381/67
(Continued)

FOREIGN PATENT DOCUMENTS

CN 107184231 A 9/2017
JP 2000-060847 A 2/2000
(Continued)

OTHER PUBLICATIONS

Official Communication issued in International Patent Application No. PCT/JP2019/015676, dated Jul. 2, 2019.
(Continued)

*Primary Examiner* — Olisa Anwah
(74) *Attorney, Agent, or Firm* — Keating and Bennett, LLP

(57) ABSTRACT

There is provided a biological sound measuring device that, in a contact state of being in contact with a body surface of a living body, measures a biological sound of the living body, the biological sound measuring device including: a first sound measuring instrument that is configured to measure the biological sound; a second sound measuring instrument that is configured to measure an ambient sound of the biological sound measuring device; and a controller that determines measurement accuracy of the biological sound in the first sound measuring instrument based on a difference in intensity at a predetermined specified frequency between a first sound measured by the first sound measuring instrument and a second sound measured by the second sound measur-
(Continued)

ing instrument, and that performs notification when the measurement accuracy is less than a predetermined value.

7 Claims, 5 Drawing Sheets

(51) Int. Cl.
*G08B 21/18* (2006.01)
*G10L 25/66* (2013.01)

(56) References Cited

U.S. PATENT DOCUMENTS

| | | | | |
|---|---|---|---|---|
| 6,375,623 | B1* | 4/2002 | Gavriely | A61B 5/1135 |
| | | | | 600/529 |
| 9,770,224 | B2* | 9/2017 | Park | H04R 1/46 |
| 9,848,848 | B2* | 12/2017 | Emmanouilidou | A61B 7/003 |
| 10,231,691 | B2* | 3/2019 | Sahin | A61B 5/7405 |
| 10,413,271 | B2* | 9/2019 | Tsai | A61B 7/04 |
| 10,765,399 | B2* | 9/2020 | Emmanouilidou | G06N 99/00 |
| 2004/0032957 | A1 | 2/2004 | Mansy et al. | |
| 2004/0228494 | A1* | 11/2004 | Smith | A61B 7/04 |
| | | | | 381/67 |
| 2007/0013509 | A1 | 1/2007 | Lakshmanan et al. | |
| 2007/0282174 | A1 | 12/2007 | Sabatino | |
| 2008/0013747 | A1* | 1/2008 | Tran | A61B 7/04 |
| | | | | 381/67 |
| 2008/0219464 | A1* | 9/2008 | Smith | G10K 15/02 |
| | | | | 381/67 |
| 2011/0034831 | A1 | 2/2011 | Christensen et al. | |
| 2012/0059280 | A1 | 3/2012 | Horii | |
| 2013/0041278 | A1* | 2/2013 | Bai | A61B 7/026 |
| | | | | 600/529 |
| 2013/0131465 | A1 | 5/2013 | Yamamoto et al. | |
| 2015/0099998 | A1 | 4/2015 | Christensen et al. | |
| 2016/0007923 | A1 | 1/2016 | Yamamoto | |
| 2018/0177482 | A1 | 6/2018 | Hashino et al. | |
| 2021/0196226 | A1* | 7/2021 | Ohgami | A61B 7/003 |

FOREIGN PATENT DOCUMENTS

| | | |
|---|---|---|
| JP | 2011-505997 A | 3/2011 |
| JP | 2012-024391 A | 2/2012 |
| JP | 2015-020030 A | 2/2015 |
| JP | 2017-074190 A | 4/2017 |
| WO | 2011/114669 A1 | 9/2011 |

OTHER PUBLICATIONS

Official Communication issued in corresponding Chinese Patent Application No. 201980025622.0, dated Nov. 17, 2021.

* cited by examiner

BIOLOGICAL SOUND MEASURING DEVICE, BIOLOGICAL SOUND MEASUREMENT SUPPORT METHOD, AND BIOLOGICAL SOUND MEASUREMENT SUPPORT PROGRAM

CROSS-REFERENCE TO RELATED APPLICATIONS

This application is a continuation of PCT application No. PCT/JP2019/015676, which was filed on Apr. 10, 2019 based on Japanese Patent Application No. 2018-078018 filed on Apr. 13, 2018, the contents of which are incorporated herein by way of reference.

BACKGROUND

The present invention relates to a biological sound measuring device that is to be brought into contact with a body surface of a living body so as to be used, and a biological sound measurement support method and program that supports measurement of a biological sound performed by the biological sound measuring device.

There has been known a device that uses a microphone to extract, as an electrical signal, a biological sound such as a respiratory sound as a sound of an airflow for ventilating the airway and the alveoli, adventitious sound that is an abnormal sound during breathing which is generated in pathological conditions such as wheezing or pleural friction, or a cardiac sound.

Patent Literature 1 discloses that a state of a device being in close contact with a body surface is determined using a light source and a photometer that are provided at a portion of the device which is in contact with the body surface.

Patent Literature 2 discloses that a state of a device being pressed against a body surface is determined using a contact sensor provided at a portion of the device which is in contact with the body surface.

Patent Literature 3 discloses that an optimum wearing position of a device is determined by comparing a plurality of sounds measured at different positions by one microphone, or by comparing a plurality of sounds measured by a plurality of microphones attached at different positions.

Patent Literature 1: JP-A-2017-74190
Patent Literature 2: JP-A-2015-20030
Patent Literature 3: JP-A-2012-24391

For a biological sound measuring device that measures a biological sound necessary for diagnosis of a living body, improvement of measurement accuracy of the biological sound is required. In Patent Literatures 1 and 2, whether or not a contact state between the device and the living body is in a state where the measurement accuracy can be secured is determined using a physical means such as a light source and a photometer, or a contact sensor. However, if the device is provided with these means, an increase in size of the device cannot be avoided. In addition, the manufacturing cost of the device increases.

In Patent Literature 3, the optimum wearing position of the device is determined by comparing two measured sounds. However, even if a wearing position of the device is optimal, mixing of sounds from the outside may increase depending on a wearing state, and measurement of the biological sound may not be performed with high accuracy.

SUMMARY

The present invention has been made in view of the above circumstances, and an object thereof is to provide a biological sound measuring device, a biological sound measurement support method, and a biological sound measurement support program capable of supporting accurate measurement of a biological sound without causing an increase in size and manufacturing cost of the device.

According to one aspect of the present invention, there is provided a biological sound measuring device that, in a contact state of being in contact with a body surface of a living body, measures a biological sound of the living body. The biological sound measuring device includes: a first sound measuring instrument that is disposed in a space sealed by the body surface in the contact state and that is configured to measure the biological sound; a second sound measuring instrument that is provided outside the space and that is configured to measure an ambient sound of the biological sound measuring device; and a controller that determines measurement accuracy of the biological sound in the first sound measuring instrument based on a difference in intensity at a predetermined specified frequency between a first sound measured by the first sound measuring instrument and a second sound measured by the second sound measuring instrument, and that performs notification when the measurement accuracy is less than a predetermined value.

According to other aspect of the present invention, the specified frequency is selected from a frequency range of 10 Hz or more and 200 Hz or less.

According to other aspect of the present invention, the specified frequency is selected from a frequency range greater than 1 kHz and equal to or less than 7 kHz.

According to other aspect of the present invention, the controller determines that the measurement accuracy is less than the predetermined value when an absolute value of a difference between an intensity of the first sound at the specified frequency and an intensity of the second sound at the specified frequency is less than a predetermined threshold, and determines that the measurement accuracy is equal to or greater than the predetermined value when the absolute value is equal to or greater than the predetermined threshold.

According to other aspect of the present invention, the controller performs the notification by outputting a message to prompt to change a way of pressing the biological sound measuring device against the body surface.

According to other aspect of the present invention, there is provided a biological sound measurement support method for supporting measurement of a biological sound performed by a biological sound measuring device that, in a contact state of being in contact with a body surface of a living body, measures a biological sound of the living body. The biological sound measuring device includes: a first sound measuring instrument that is disposed in a space sealed by the body surface in the contact state and that is configured to measure the biological sound; and a second sound measuring instrument that is provided outside the space and that is configured to measure an ambient sound of the biological sound measuring device. The biological sound measurement support method includes: a control step of determining measurement accuracy of the biological sound in the first sound measuring instrument based on a difference in intensity at a predetermined specified frequency between a first sound measured by the first sound measuring instrument and a second sound measured by the second sound measuring instrument, and performing notification when the measurement accuracy is less than a predetermined value.

According to other aspect of the present invention, there is provided a storage medium which stores biological sound measurement support program for supporting measurement of a biological sound performed by a biological sound measuring device that, in a contact state of being in contact with a body surface of a living body, measures a biological sound of the living body. The biological sound measuring device includes: a first sound measuring instrument that is disposed in a space sealed by the body surface in the contact state and that is configured to measure the biological sound; and a second sound measuring instrument that is provided outside the space and that is configured to measure an ambient sound of the biological sound measuring device. The biological sound measurement support program causes a computer to execute a control step of: determining measurement accuracy of the biological sound in the first sound measuring instrument based on a difference in intensity at a predetermined specified frequency between a first sound measured by the first sound measuring instrument and a second sound measured by the second sound measuring instrument, and performing notification when the measurement accuracy is less than a predetermined value.

Figure 1:
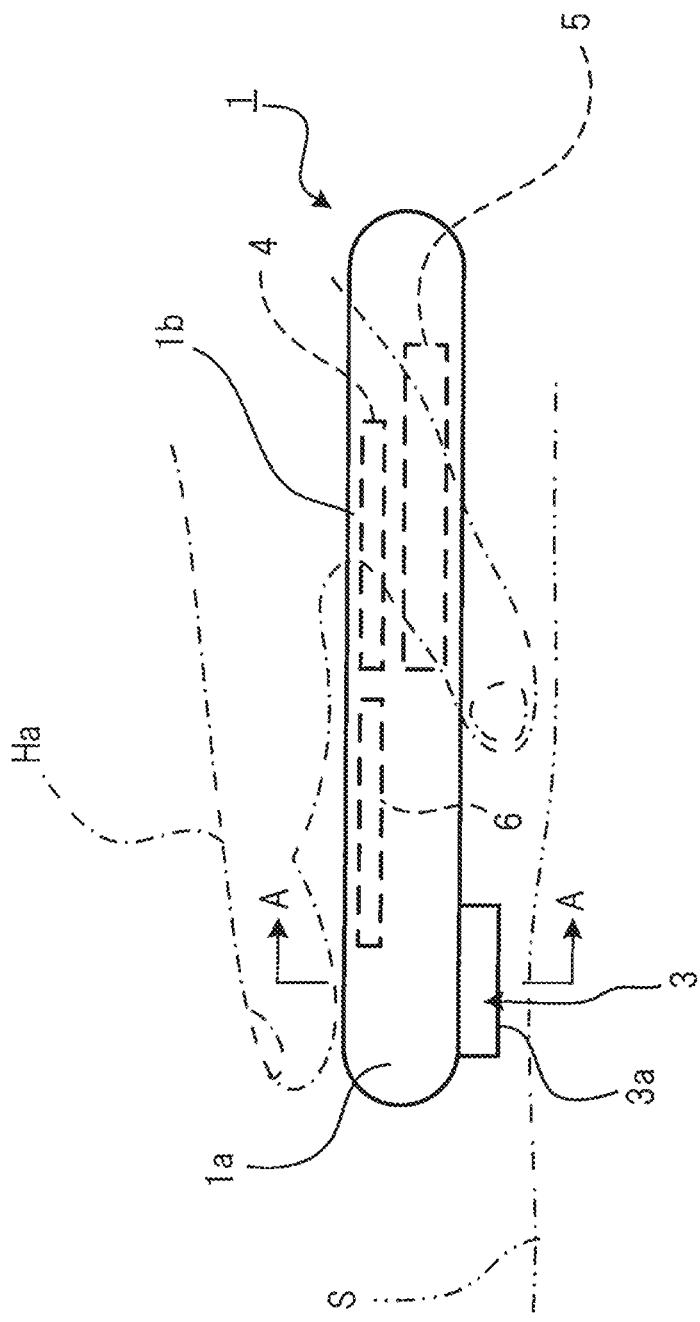
FIG. 1 is a side view illustrating a schematic configuration example of a biological sound measuring device 1 as an embodiment of a biological sound measuring device of the present invention.

DESCRIPTION OF EMBODIMENTS (Outline of Biological Sound Measuring Device of Embodiment)

First, an outline of an embodiment of a biological sound measuring device of the present invention will be described. The biological sound measuring device of the embodiment measures a pulmonary sound (a respiratory sound and adventitious sound) as an example of a biological sound from a human living body, and when it is determined that wheezing is included in a measured sound, the biological sound measuring device reports that. In this way, support is given in determination of whether to give medicine to the subject, determination of whether to bring the subject to a hospital, or diagnosis for the subject by a doctor.

The biological sound measuring device of the embodiment includes a first sound measuring instrument that is configured to measure a pulmonary sound and a second sound measuring instrument that is configured to measure an ambient sound of the device. The biological sound measuring device measures a pulmonary sound of a living body using the first sound measuring instrument by sealing a space in which the first sound measuring instrument is accommodated with a body surface. The second sound measuring instrument is used, for example, to remove noise included in the sound to be measured by the first sound measuring instrument other than the pulmonary sound.

In a state where the biological sound measuring device of the embodiment is not ideally in contact with the body surface of the living body (for example, a state where the accommodation space of the first sound measuring instrument is not completely sealed), substantially the same sound is measured by the first sound measuring instrument and the second sound measuring instrument. Therefore, an intensity of the sound measured by the first sound measuring instrument and an intensity of the sound measured by the second sound measuring instrument are substantially the same at any frequency.

On the other hand, in an optimum state where the biological sound measuring device is ideally in contact with the body surface of the living body (for example, a state where the accommodation space of the first sound measuring instrument is sealed by the body surface), the intensity of the sound measured by the first sound measuring instrument and the intensity of the sound measured by the second sound measuring instrument differ depending on the frequency.

Specifically in the optimum state, since the first sound measuring instrument mainly measures the pulmonary sound, an intensity regarding a frequency of the pulmonary sound is higher than when it is not the optimum state. On the other hand, the second sound measuring instrument is not in a sealed state with the body surface, and cannot measure the pulmonary sound. Therefore, among the sounds measured by the second sound measuring instrument, an intensity regarding a frequency of the pulmonary sound is low even in the optimum state.

Therefore, when a difference between an intensity of a sound at a specified frequency (for example, a frequency selected from a frequency range of the pulmonary sound) measured by the first sound measuring instrument and an intensity of the sound at the specified frequency measured by the second sound measuring instrument is large, it can be determined that measurement accuracy of the pulmonary sound is sufficiently obtained.

The biological sound measuring device of the embodiment uses this to determine the measurement accuracy of the pulmonary sound. When the measurement accuracy is less than a predetermined value, for example, the biological sound measuring device performs notification of prompting to change the way of pressing the device against the body surface, thereby supporting accurate measurement of the pulmonary sound. Hereinafter, a specific configuration example of the biological sound measuring device of the embodiment will be described.

(Embodiment)

FIG. 1 is a side view illustrating a schematic configuration example of a biological sound measuring device 1 as an embodiment of the biological sound measuring device of the present invention.

As illustrated in FIG. 1, the biological sound measuring device 1 includes a main body 1b formed of a housing made of resin, metal, or the like, and a head portion 1a is provided on one end side of the main body 1b.

Inside the main body 1b, a controller 4 that performs overall control of the whole, a battery 5 that supplies a voltage required for operation, and a display unit 6 that displays an image by a liquid crystal display panel, an organic electro luminescence (EL) display panel or the like are provided.

The controller 4 includes a central processing unit (CPU), a random access memory (RAM), a read only memory (ROM), and the like, and controls hardware of the biological sound measuring device 1 in accordance with a program. Programs including a biological sound measurement support program are stored in the ROM of the controller 4.

The head portion 1a is provided with a measuring unit 3 protruding toward one side (lower side in FIG. 1) in a direction substantially orthogonal to a longitudinal direction of the biological sound measuring device 1. A pressure receiving portion 3a that is to be brought into contact with a body surface S of a living body, which is a subject, to receive a pressure from the body surface S is provided at a front end of the measuring unit 3.

In using the biological sound measuring device 1, a user places, for example, an index finger of his/her hand Ha on a back surface of the measuring unit 3 in the head portion 1a, and presses the pressure receiving portion 3a of the measuring unit 3 against the body surface S with the index finger.

Figure 2:
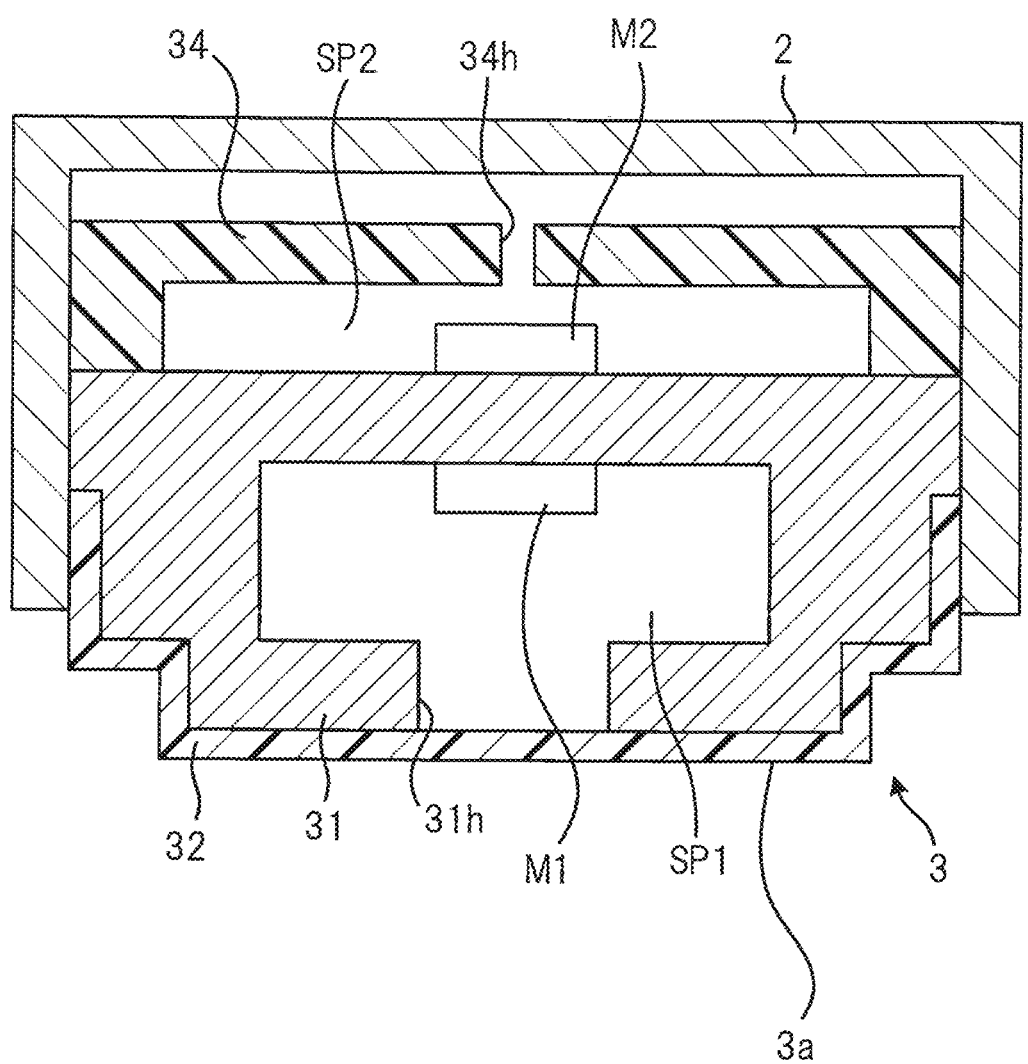
FIG. 2 is a schematic cross-sectional view of the biological sound measuring device 1 taken along a line A-A in FIG. 1.

FIG. 2 is a schematic cross-sectional view of the biological sound measuring device 1 taken along a line A-A in FIG. 1.

The measuring unit 3 includes: a first sound measuring instrument M1 that measures a sound; a first housing 31 that forms an accommodation space SP1 for accommodating the first sound measuring instrument M1 and that has an opening 31h; a housing cover 32 that closes the opening 31h from an outer side of the accommodation space SP1 and that covers the first housing 31; a second sound measuring instrument M2 that measures a sound; and a second housing 34 that forms an accommodation space SP2 for accommodating the second sound measuring instrument M2 and that has an opening 34h.

The measuring unit 3 is fitted into an opening portion formed in a housing 2 constituting the head portion 1a, with a part of the housing cover 32 being exposed, and is fixed to the housing 2.

A front end portion of the part of the housing cover 32, which is exposed from the housing 2, is a flat surface, and this flat surface constitutes the pressure receiving portion 3a in FIG. 1. The housing 2 is made of resin or the like capable of transmitting a sound.

The first sound measuring instrument M1 is configured to measure a pulmonary sound to be measured by the biological sound measuring device 1, and is configured with, for example, a micro electro mechanical systems (MEMS) microphone or a capacitance-type microphone that measures a sound in a frequency band (for example, a frequency range of 10 Hz or more and 10 kHz or less) wider than a frequency range of pulmonary sound (generally, 10 Hz or more and 1 kHz or less).

The first sound measuring instrument M1 is electrically connected to the controller 4 illustrated in FIG. 1 by a lead wire or the like (not illustrated), and transmits information on a measured sound to the controller 4.

At the time of using the biological sound measuring device 1, a state is established where the pressure receiving portion 3a of the housing cover 32 comes into contact with the body surface S and the accommodation space SP1 is sealed by the body surface S under a pressure from the body surface S (hereinafter, this state is referred to as a contact state).

Further, when the pressure receiving portion 3a vibrates due to the pulmonary sound transmitted from the living body to the body surface S, an internal pressure of the accommodation space SP1 fluctuates due to this vibration, and an electrical signal corresponding to the pulmonary sound is measured by the first sound measuring instrument M1 based on the fluctuation of the internal pressure.

The first housing 31 has a substantially convex shape directed in a lower direction in FIG. 2, and is made of a material having higher acoustic impedance than air and having higher rigidity, such as a resin or a metal. The first housing 31 is made of a material that reflects sounds in measurement frequency bands of the first sound measuring instrument M1 and the second sound measuring instrument M2 so that the sounds are not transmitted from the outside into the accommodation space SP1 in the contact state.

The housing cover 32 is a bottomed cylindrical member, and a shape of a hollow portion thereof substantially coincides with a shape of an outer wall of the first housing 31.

The housing cover 32 is made of a material having acoustic impedance close to that of a human body, air, or water, and having good flexibility and good biocompatibility. As a material of the housing cover 32, for example, silicon, an elastomer, or the like is used.

The second sound measuring instrument M2 is configured to measure a sound generated around the biological sound measuring device 1 (an environmental sound such as human speech, or a sound generated due to rubbing between the main body 1b and the living body or clothing), and is configured with, for example, an MEMS microphone or a capacitance-type microphone that measures a sound in a band (for example, a frequency range of 10 Hz or more and 10 kHz or less) wider than the frequency range of pulmonary sound.

The second sound measuring instrument M2 is electrically connected to the controller 4 illustrated in FIG. 1 by a lead wire or the like (not illustrated), and transmits information on a measured sound to the controller 4.

The second sound measuring instrument M2 is fixed to a surface of the first housing 31, opposite from the pressure receiving portion 3a. A periphery of the second sound measuring instrument M2 is covered with the second housing 34. The second housing 34 is made of a material (for example, a resin) that allows a sound generated around the biological sound measuring device 1 to enter the accommodation space SP2 for accommodating the second sound measuring instrument M2.

The opening 34h is formed in the second housing 34. Therefore, a structure is formed in which the sound generated around the biological sound measuring device 1 easily enters from the opening 34h.

Although the second sound measuring instrument M2 is provided in the measuring unit 3 in the example of FIG. 2, the installation location is not particularly limited as long as the sound generated around the biological sound measuring device 1 can be measured. For example, the second sound measuring instrument M2 may be provided at a place of the main body 1b, which the user is unlikely to touch during use, other than the head portion 1a.

The controller 4 illustrated in FIG. 1 determines measurement accuracy of the pulmonary sound in the first sound measuring instrument M1, based on a difference in intensity at a predetermined specified frequency between a first sound measured by the first sound measuring instrument M1 and a second sound measured by the second sound measuring instrument M2.

As the specified frequency, a frequency at which the intensity of the sound detected by the first sound measuring instrument M1 in the contact state is significantly higher or lower than in a non-contact state is used.

Figure 3:
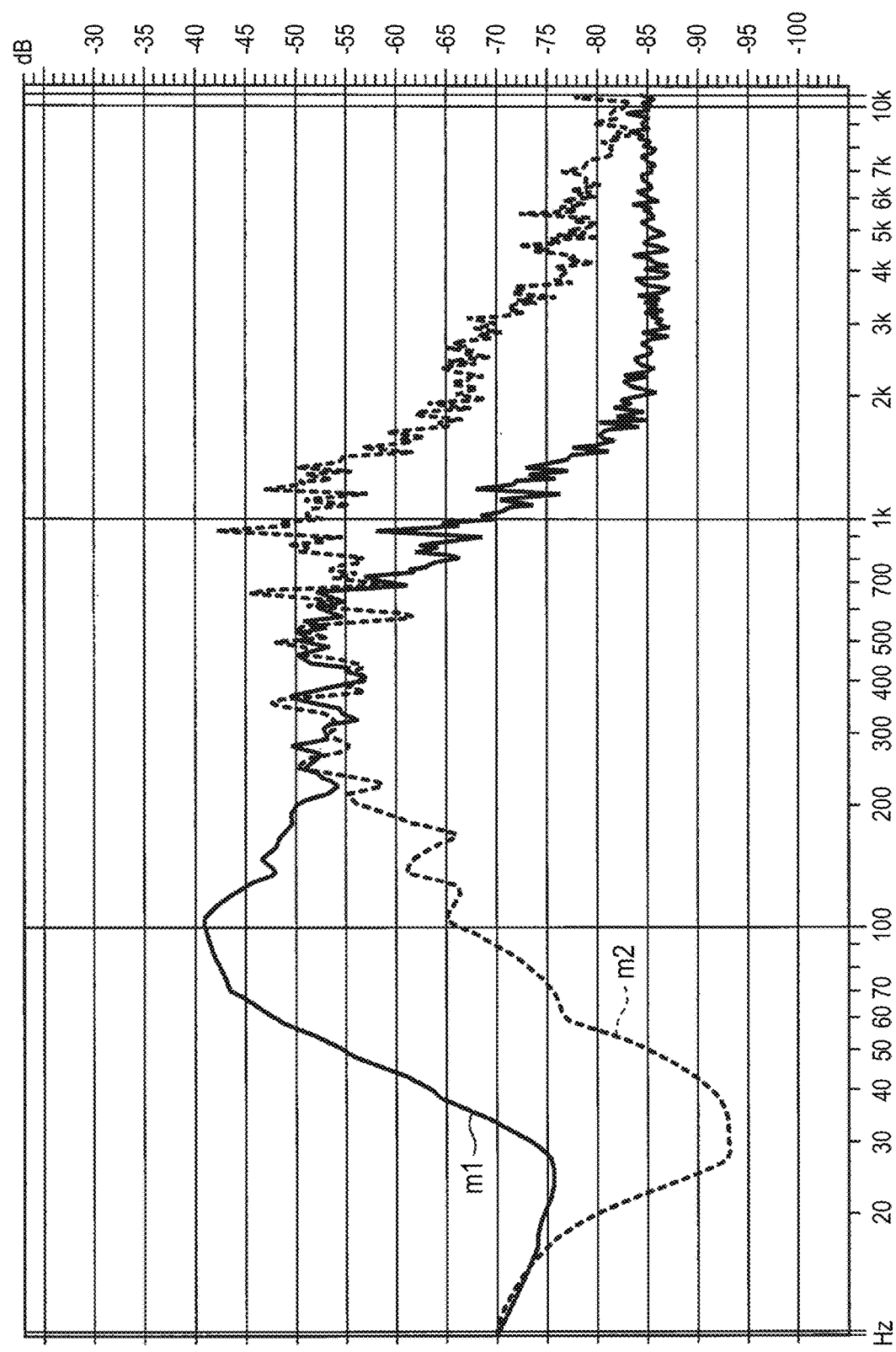
FIG. 3 is a graph showing Fourier transform results of sounds measured by a first sound measuring instrument M1 and a second sound measuring instrument M2 in a contact state of the biological sound measuring device 1 shown in FIG. 1.

FIG. 3 is a graph showing Fourier transform results of sounds measured by the first sound measuring instrument M1 and the second sound measuring instrument M2 in a contact state of the biological sound measuring device 1 shown in FIG. 1.

Figure 4:
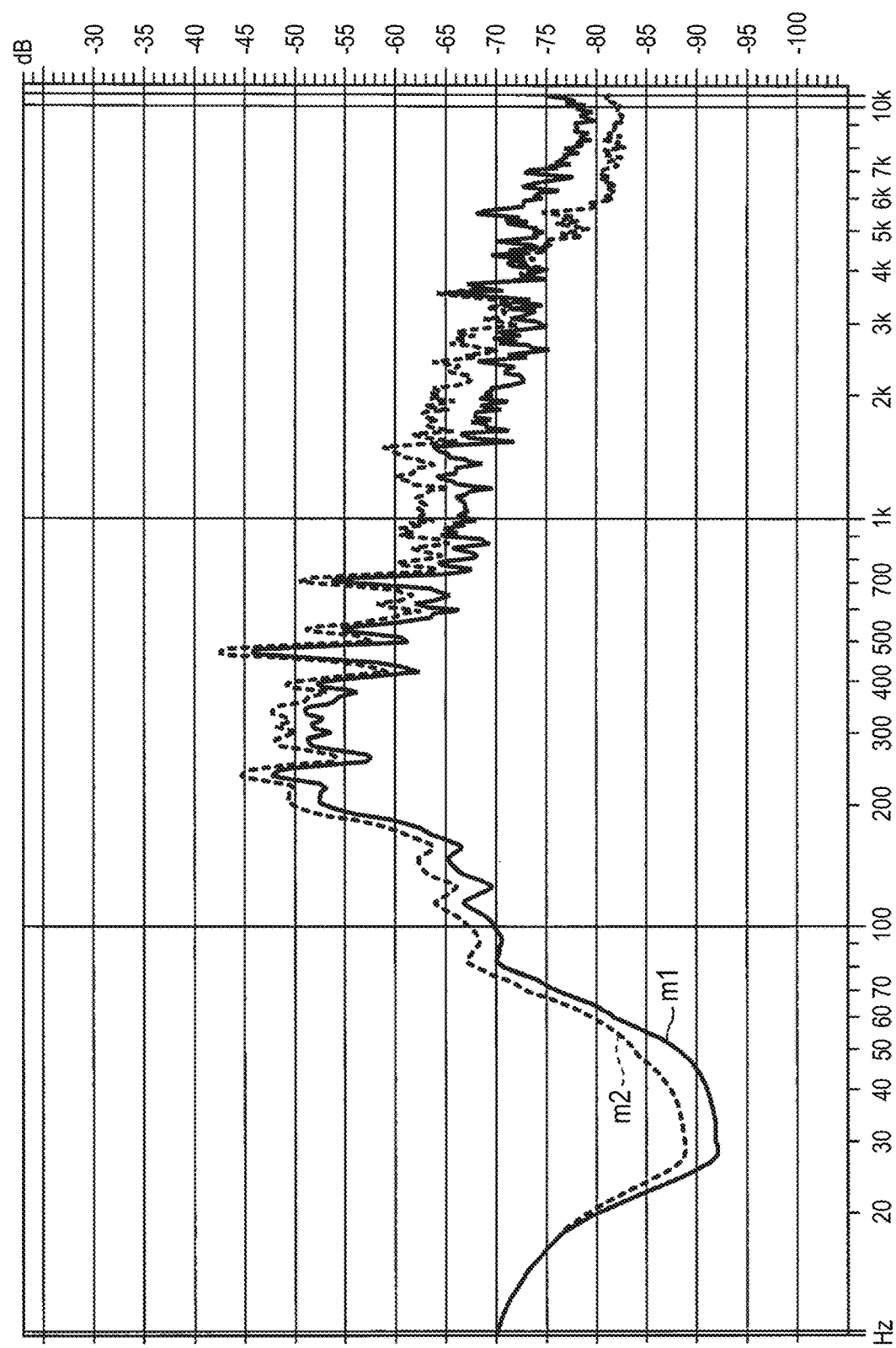
FIG. 4 is a graph showing Fourier transform results of sounds measured by the first sound measuring instrument M1 and the second sound measuring instrument M2 in a non-contact state of the biological sound measuring device 1 shown in FIG. 1.

FIG. 4 is a graph showing Fourier transform results of sounds measured by the first sound measuring instrument M1 and the second sound measuring instrument M2 in a non-contact state of the biological sound measuring device 1 shown in FIG. 1.

FIGS. 3 and 4 each show a graph m1 obtained by performing Fourier transform on the first sound measured by the first sound measuring instrument M1 and a graph m2 obtained by performing Fourier transform on the second sound measured by the second sound measuring instrument M2. In FIGS. 3 and 4, the horizontal axis indicates the frequency in logarithm.

As shown in FIG. 4, in the non-contact state, substantially the same sounds are measured by the first sound measuring instrument M1 and the second sound measuring instrument M2. Therefore, there is little difference between the graph m1 and the graph m2.

On the other hand, in the contact state, the pulmonary sound is transmitted to the accommodation space SP1 of the first sound measuring instrument M1, and the pulmonary sound is not transmitted to the accommodation space SP2. Therefore, as shown in FIG. 3, the difference between the intensity of the sound measured by the first sound measuring instrument M1 and the intensity of the sound measured by the second sound measuring instrument M2 is increased in a frequency range of 20 Hz or more and 200 Hz or less.

As described above, the intensity of the sound in the frequency range of 20 Hz or more and 200 Hz or less detected by the first sound measuring instrument M1 is remarkably increased in the contact state. In the examples of FIGS. 3 and 4, the difference between the intensity of the sound measured by the first sound measuring instrument M1 and the intensity of the sound measured by the second sound measuring instrument M2 is reduced in a frequency range of less than 20 Hz. However, this is one example, and in the contact state, the intensity of sound in a low frequency range (for example, 10 Hz or more and 200 Hz or less), which is less likely to be generated outside the accommodation space SP1, in the frequency range of the pulmonary sound is remarkably increased. Therefore, for example, an arbitrary frequency (for example, 50 Hz and 100 Hz) selected from a frequency range of 10 Hz or more and 200 Hz or less can be set as the specified frequency. Based on the results of FIGS. 3 and 4, it is preferable to set an arbitrary frequency selected from the frequency range of 20 Hz or more and 200 Hz or less as the specified frequency, and it is more preferable to set an arbitrary frequency selected from a frequency range of 30 Hz or more and 150 Hz or less, in which the difference between the two graphs is more remarkable, as the specified frequency.

In the contact state, entry of sounds from the outside into the accommodation space SP1 of the first sound measuring instrument M1 is greatly reduced. Therefore, as shown in FIG. 3, the difference between the intensity of the sound measured by the first sound measuring instrument M1 and the intensity of the sound measured by the second sound measuring instrument M2 is increased in a frequency range greater than 1 kHz and equal to or less than 7 kHz, which is higher than the frequency range of the pulmonary sound.

As described above, the intensity of the sound in the frequency range greater than 1 kHz and equal to or less than 7 kHz detected by the first sound measuring instrument M1 is remarkably reduced in the contact state. Therefore, for example, an arbitrary frequency (for example, 1.5 kHz and 2 kHz) selected from the frequency range of greater than 1 kHz and equal to or less than 7 kHz can be set as the specified frequency.

The specified frequencies and the frequency ranges from which the specified frequencies are selected are appropriately determined depending on a type of the biological sound to be measured, and are not limited to the values described above.

When the specified frequency is set as described above, in the contact state, the difference in the intensity at the specified frequency between the first sound measured by the first sound measuring instrument M1 and the second sound measured by the second sound measuring instrument M2 is significantly larger than that in the case of non-contact state (the state where substantially the same sound is measured by the first sound measuring instrument M1 and the second sound measuring instrument M2).

Accordingly, the controller 4 determines that the measurement accuracy of the first sound is less than the predetermined value when an absolute value of the difference between the intensity of the first sound at the specified frequency and the intensity of the second sound at the specified frequency is less than a predetermined threshold. And the controller 4 determines that the measurement accuracy of the first sound is equal to or greater than the predetermined value when the absolute value is equal to or greater than the predetermined threshold.

When it is determined that the measurement accuracy is less than the predetermined value, the controller 4 performs notification. For example, the controller 4 performs notification by causing the display unit 6 to display a message to prompt to change the way of pressing the pressure receiving portion 3a against the body surface S. The controller 4 may perform notification by outputting the message from a speaker (not illustrated).

The biological sound measuring device 1 may be configured to be connectable to, for example, a smartphone, and display or audio output of the message may be performed using a display or a speaker of the smartphone.

Here, output of the message is performed, but the present invention is not limited thereto. For example, a light emitting diode (LED) may be mounted on the biological sound measuring device 1, and the controller 4 may cause the LED to emit, for example, blue light when it is determined that the measurement accuracy is equal to or greater than the predetermined value, and notify the user of checking whether the way of pressing is fine or not by causing the LED to emit, for example, red light when it is determined that the measurement accuracy less than the predetermined value.

Even in such a case, by describing meaning of emission colors of the LED in a manual or the like attached to the biological sound measuring device 1, it is possible to prompt the user to change the way of pressing.

(Operation Example of Biological Sound Measuring Device 1)

Figure 5:
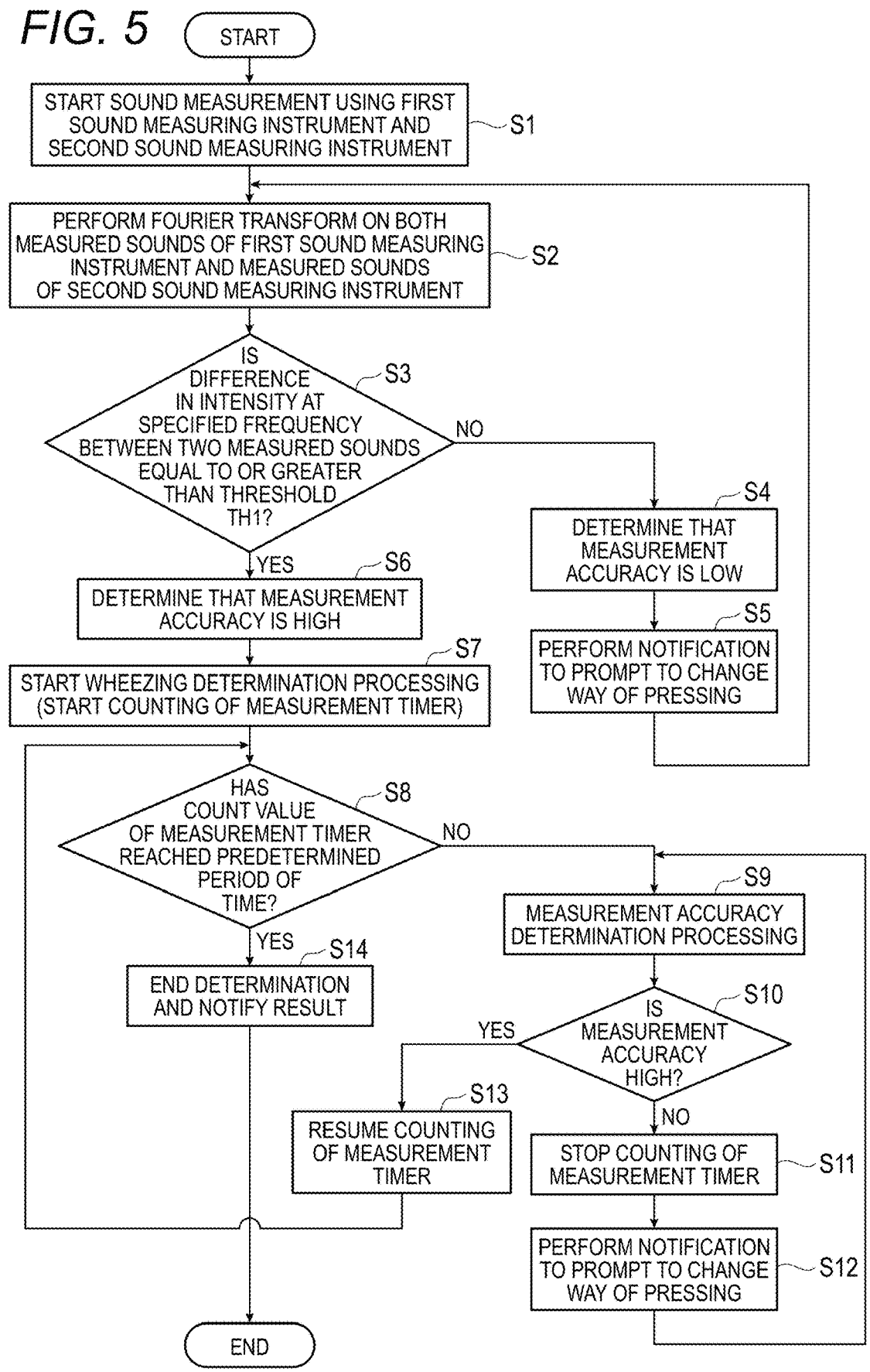
FIG. 5 is a flowchart for illustrating an operation example of the biological sound measuring device 1 shown in FIG. 1.

FIG. 5 is a flowchart for illustrating an operation example of the biological sound measuring device 1 illustrated in FIG. 1.

When the biological sound measuring device 1 is powered on, the controller 4 causes sound measurement to be performed by the first sound measuring instrument M1 and the second sound measuring instrument M2 to start (step S1). Information on sounds measured by the first sound measuring instrument M1 and the second sound measuring instrument M2 is stored in the RAM of the controller 4.

Further, when a predetermined period of time elapses, the controller 4 performs Fourier transform on both the first sounds and the second sounds collected over the predetermined period of time which are stored in the RAM (step S2).

Next, the controller 4 obtains an absolute value of a difference between an intensity of a first sound at a specified frequency which is obtained by the Fourier transform and an intensity of a second sound at the specified frequency which is obtained by the Fourier transform, and determines whether or not the absolute value is equal to or greater than a predetermined threshold TH1 (step S3).

For example, a case where the specified frequency is selected from a frequency range of 20 Hz or more and 200 Hz or less will be described. In this case, for example, the threshold TH1 is set to a largest value among or an average value of differences between the intensity of each frequency in the range of 20 Hz or more and 200 Hz or less of the graph m1 shown in FIG. 4 and the intensity of each frequency in the range of 20 Hz or more and 200 Hz or less of the graph m2 shown in FIG. 4.

Further, a case where the specified frequency is selected from a frequency range greater than 1 kHz and equal to or less than 7 kHz will be described. In this case, for example, the threshold TH1 is set to a largest value among or an average value of differences between the intensity of each frequency in the range greater than 1 kHz and equal to or less than 7 kHz of the graph m1 shown in FIG. 4 and the intensity of each frequency in the range greater than 1 kHz and equal to or less than 7 kHz of the graph m2 shown in FIG. 4.

When the absolute value is less than the threshold TH1 (step S3: NO), the controller 4 determines that the measurement accuracy of the sound in the first sound measuring instrument M1 is low (less than the predetermined value) (step S4).

After step S4, the controller 4 performs notification to prompt to change a way of pressing the pressure receiving portion 3a, for example (step S5). After step S5, the process returns to step S2, and the processing of step S2 is performed at a time point when sounds are measured again over the predetermined period of time.

When the absolute value is equal to or greater than the threshold TH1 (step S3: YES), the controller 4 determines that the measurement accuracy of the sound in the first sound measuring instrument M1 is high (equal to or greater than the predetermined value) (step S6).

After step S6, the controller 4 starts to perform up-counting of a count value of a built-in measurement timer, and starts determination processing of determining presence or absence of wheezing (step S7).

Specifically, the controller 4 removes noise, other than the pulmonary sound, which is mixed in the first sound measured by the first sound measuring instrument M1, based on the second sound measured by the second sound measuring instrument M2. Further, the controller 4 determines that "wheezing is present" when, for example, the first sound after the noise removal has an intensity equal to or greater than an intensity at which a sound can be determined to be wheezing.

After starting the determination processing of determining presence or absence of wheezing in step S7, the controller 4 determines whether or not the count value of the measurement timer has reached a predetermined period of time necessary for determining the presence or absence of wheezing (step S8).

When the count value has not reached the predetermined period of time (step S8: NO), the controller 4 performs the determination processing of the measurement accuracy which is described in step S2, step S3, step S4, and step S6, based on data of the sound which is accumulated in the RAM after the determination of the measurement accuracy is performed at a previous time (step S9).

As a result of the determination processing in step S9, when the measurement accuracy is less than the predetermined value (step S10: NO), the controller 4 temporarily stops the up-counting of the measurement timer (step S11), and thereafter performs notification to prompt to change the way of pressing the pressure receiving portion 3a (step S12). After step S12, the process returns to step S9.

As a result of the determination processing in step S9, when the measurement accuracy is equal to or greater than the predetermined value (step S10: YES), the controller 4 resumes the up-counting of the count value of the measurement timer (step S13). The processing of step S13 is executed only in a case where the processing of step S11 is performed after the determination in step S8 is "NO". After step S13, the process returns to step S8.

When the count value has reached the predetermined period of time in step S8 (step S8: YES), the controller 4 ends the determination processing of determining presence or absence of wheezing and displays a determination result thereof on, for example, the display unit 6 (step S14), and ends the measurement.

(Effects of Biological Sound Measuring Device 1)

As described above, according to the biological sound measuring device 1, the measurement accuracy of the pulmonary sound in the first sound measuring instrument M1 can be determined based on the difference in intensity at the specified frequency between the sound measured by the first sound measuring instrument M1 and the sound measured by the second sound measuring instrument M2.

Since it is unnecessary to provide the second sound measuring instrument M2 in the vicinity of the pressure receiving portion 3a, it is possible to prevent a structure in the vicinity of the pressure receiving portion 3a from becoming large and complex. In addition, since the second sound measuring instrument M2 does not have the restriction of being accommodated in a sealed state or the like, reduction of a size of the device is not hindered.

Furthermore, since the second sound measuring instrument M2 can also be used in removing noise at the time of measuring the pulmonary sound, it is possible to prevent an increase in manufacturing cost of the device as compared with a case where a dedicated sound measuring instrument is provided for determining the measurement accuracy.

Although the second sound measuring instrument M2 is also used in removing noise in the above example, the second sound measuring instrument M2 may be provided only for determining the measurement accuracy.

Further, according to the biological sound measuring device 1, since the determination processing of determining presence or absence of wheezing is started when it is determined by the controller 4 that the measurement accuracy is high, the presence or absence of wheezing can be determined with high accuracy.

When it is determined that the measurement accuracy has decreased after start of the determination processing of determining presence or absence of wheezing, the notification is performed again. Therefore, the user can change the way of pressing the device in accordance with the notification, and a state where the measurement accuracy is high can be restored.

In addition, during a time period when it is determined that the measurement accuracy has decreased, the determination processing of determining presence or absence of wheezing is temporarily stopped, and when the state where the measurement accuracy is high is restored, the determination processing is resumed. Therefore, it is unnecessary to redo the determination processing of determining presence or absence of wheezing, and a period of time until output of the determination result of presence or absence of wheezing can be shortened.

(Modification of Biological Sound Measuring Device 1)

In step S3 of FIG. 5, one specified frequency is set and the determination of measurement accuracy is performed. However, a plurality of specified frequencies may be set.

For example, both an arbitrary frequency (for example, 100 Hz) selected from a frequency range of 10 Hz or more and 200 Hz or less, and an arbitrary frequency (for example, 2 kHz) selected from a frequency range greater than 1 kHz and equal to or less than 7 kHz can also be set as the specified frequency.

When two specified frequencies are set as described, a threshold TH1, which is to be compared with the specified frequency selected from the frequency range of 10 Hz or more and 200 Hz or less, is set to, for example, the largest value among or the average value of the differences between the intensity of each frequency in the range of 20 Hz or more and 200 Hz or less of the graph m1 shown in FIG. 4 and the intensity of each frequency in the range of 20 Hz or more and 200 Hz or less of the graph m2 shown in FIG. 4.

Further, a threshold TH1, which is to be compared with the specified frequency selected from the frequency range greater than 1 kHz and equal to or less than 7 kHz, is set to, for example, the largest value among or the average value of differences between the intensity of each frequency in the range greater than 1 kHz and equal to or less than 7 kHz of the graph m1 shown in FIG. 4 and the intensity of each frequency in the range greater than 1 kHz and equal to or less than 7 kHz of the graph m2 shown in FIG. 4.

As described above, when two specified frequencies are set, the thresholds TH1 to be compared with the two specified frequencies respectively may be set to different values.

In a case where two specified frequencies are set, when the difference in intensity between the first sound and the second sound at each of the two specified frequencies is equal to or greater than the threshold value TH1 in step S3 of FIG. 5, the controller 4 determines in step S6 that the measurement accuracy is high. When the difference in intensity between the first sound and the second sound at one of the two specified frequencies is less than the threshold TH1, the controller 4 determines in step S4 that the measurement accuracy is low.

By setting a plurality of specified frequencies in this manner, it is possible to more accurately determine the measurement accuracy.

Although an embodiment of the present invention and a modification thereof have been described above, the present invention is not limited thereto, and can be modified as appropriate. For example, although the first sound measuring instrument M1 is configured to measure the pulmonary sound as a biological sound in the embodiment and the modification described above, the first sound measuring instrument M1 may be configured to measure a cardiac sound or the like as a biological sound.

Although the embodiments are described above with reference to the drawings, it is needless to say that the present invention is not limited to such examples. It will be apparent to those skilled in the art that various changes and modifications may be conceived within the scope of the claims. It is also understood that the various changes and modifications belong to the technical scope of the present invention. Components in the embodiments described above may be combined freely within a range not departing from the spirit of the present invention.

What is claimed is:

1. A biological sound measuring device that, in a contact state of being in contact with a body surface of a living body, measures a biological sound of the living body, the biological sound measuring device comprising:
   a first sound measuring instrument that is disposed in a space sealed by the body surface in the contact state and that is configured to measure the biological sound;
   a second sound measuring instrument that is provided outside the space and that is configured to measure an ambient sound of the biological sound measuring device; and
   a controller that determines measurement accuracy of the biological sound in the first sound measuring instrument based on a difference in intensity at a predetermined specified frequency between a first sound measured by the first sound measuring instrument and a second sound measured by the second sound measuring instrument, and that performs notification when the measurement accuracy is less than a predetermined value.

2. The biological sound measuring device according to claim 1,
   wherein the specified frequency is selected from a frequency range of 10 Hz or more and 200 Hz or less.

3. The biological sound measuring device according to claim 1,
   wherein the specified frequency is selected from a frequency range greater than 1 kHz and equal to or less than 7 kHz.

4. The biological sound measuring device according to claim 1,
   wherein the controller determines that the measurement accuracy is less than the predetermined value when an absolute value of a difference between an intensity of the first sound at the specified frequency and an intensity of the second sound at the specified frequency is less than a predetermined threshold, and determines that the measurement accuracy is equal to or greater than the predetermined value when the absolute value is equal to or greater than the predetermined threshold.

5. The biological sound measuring device according to claim 1,
   wherein the controller performs the notification by outputting a message to prompt to change a way of pressing the biological sound measuring device against the body surface.

6. A biological sound measurement support method for supporting measurement of a biological sound performed by a biological sound measuring device that, in a contact state of being in contact with a body surface of a living body, measures a biological sound of the living body,
   the biological sound measuring device including: a first sound measuring instrument that is disposed in a space sealed by the body surface in the contact state and that is configured to measure the biological sound; and a second sound measuring instrument that is provided outside the space and that is configured to measure an ambient sound of the biological sound measuring device,
   the biological sound measurement support method comprising:
   a control step of determining measurement accuracy of the biological sound in the first sound measuring instrument based on a difference in intensity at a predetermined specified frequency between a first sound measured by the first sound measuring instrument and a second sound measured by the second sound measuring instrument, and performing notification when the measurement accuracy is less than a predetermined value.

7. A non-transitory computer readable storage medium which stores a biological sound measurement support program for supporting measurement of a biological sound performed by a biological sound measuring device that, in a contact state of being in contact with a body surface of a living body, measures a biological sound of the living body,
the biological sound measuring device including: a first sound measuring instrument that is disposed in a space sealed by the body surface in the contact state and that is configured to measure the biological sound; and a second sound measuring instrument that is provided outside the space and that is configured to measure an ambient sound of the biological sound measuring device,
the biological sound measurement support program causing a computer to execute a control step of: determining measurement accuracy of the biological sound in the first sound measuring instrument based on a difference in intensity at a predetermined specified frequency between a first sound measured by the first sound measuring instrument and a second sound measured by the second sound measuring instrument, and performing notification when the measurement accuracy is less than a predetermined value.

\* \* \* \* \*